(12) United States Patent
Tannenbaum

(10) Patent No.: US 7,627,434 B2
(45) Date of Patent: Dec. 1, 2009

(54) METHOD FOR FIELD-BASED ECOLOGICAL RISK ASSESSMENT USING RODENT SPERM-ANALYSIS

(75) Inventor: Lawrence V. Tannenbaum, Baltimore, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 447 days.

(21) Appl. No.: 10/820,848

(22) Filed: Apr. 9, 2004

(65) Prior Publication Data

US 2004/0234946 A1 Nov. 25, 2004

Related U.S. Application Data

(60) Provisional application No. 60/510,542, filed on Oct. 14, 2003, provisional application No. 60/461,813, filed on Apr. 11, 2003.

(51) Int. Cl.
*G01N 33/48* (2006.01)
(52) U.S. Cl. .................................................. 702/19
(58) Field of Classification Search .................. 702/19
See application file for complete search history.

(56) References Cited

OTHER PUBLICATIONS

Sharma et al. "Reversible Effect of Mercuric Chloride on Reproductive Organs of the Male Mouse," Reproductive Toxicology (1996) vol. 10, No. 2, pp. 153-159.*
Ieradi et al. "Genetic Damage in Urban Mice Exposed to Traffice Pollution," Environmental Pollution (1996) vol. 92, No. 3, pp. 323-328.*
Phillips et al. "Assessment of Potential Environmental Health Risks of Residue of High-Explosive Munitions on Military Test Ranges—Comparison in a Humid and Arid Climate," Federal Facilities Environmental Journal (2002) vol. 13, Issue 1, pp. 7-25.*
Ieradi et al."Evaluation of Genotoxic Damage in Wild Rodents From a Polluted Area in the Czech Republic," Folia Zoologica (Jan. 2003) vol. 52, No. 1, pp. 57-66.*
Ryabokon et al. "Long-Term Development of the Radionuclide Exposure of Murine Rodent Populations in Belarus after the Chernobyl Accident," Radiat. Environ. Biophys (2005) vol. 44, pp. 169-181.*
Working, Peter "Male Reproductive Toxicology: Comparison of the Human to Animal Models," Environmental Health Perspectives (1988) vol. 77, pp. 37-44.*
Bucci, L.R., et al., "Effects of busulfan on murine spermatogenesis: cytotoxicity, sterility, sperm abnormalities, and dominant lethal mutations," MutationResearch, 1987, p. 259-268, vol. 176.
Chapin, Robert, E., et al., "The Relationships among Reproductive Endpoints in Swiss Mice, Using the Reproductive Assessment by Continuous Breeding Database," Fundamental and Applied Toxicology, 1997, pp. 129-142, vol. 38.
Gray, et al., "Correlation of Ejaculated Sperm Numbers with Fertility In the Rat," Toxicologist, 1992, p. 633, vol. 12.
Meistrich, Marvin L., et al., "Deficiency in Fertilization by Morphologically Abnormal Sperm Produced by azh Mutant Mice," Molecular Reproduction and Development, 1994, pp. 69-77, vol. 37.
Tannenbaum, et al., "Rodent sperm analysis in field-based ecological risk assessment: pilot study at Ravenna army ammunition plant, Ravenna, Ohio," Environmental Pollution, May 2003, pp. 21-29, vol. 123.
Sample, B.E., et al., "Toxicological Benchmarks for Wildlife: 1996 Revision," Risk Assessment Program Health Sciences Research Division, Jun. 1996.

* cited by examiner

*Primary Examiner*—Jerry Lin
(74) *Attorney, Agent, or Firm*—Elizabeth Arwine

(57) ABSTRACT

The invention is a method for assessing whether or not reproductive health effects are present in terrestrial ecological receptors inhabiting contaminated sites. Adult male rodents are concurrently trapped at the contaminated site of interest and at a matched non-contaminated reference location. In at least some embodiments, the sperm analysis can be corroborated with additional data to further increase the accuracy of the comparison. For a given small rodent species, three sperm parameters, all of which are barometers of reproductive success (a high concern ecological risk assessment toxicological endpoint), are compared in the animals trapped at the contaminated site and the animals trapped at the reference location. Where one or more of the sperm parameter thresholds are exceeded in the site rodents, and the difference is found to be statistically significant, the interpretation is that site terrestrial receptors are being reproductively compromised.

22 Claims, 3 Drawing Sheets

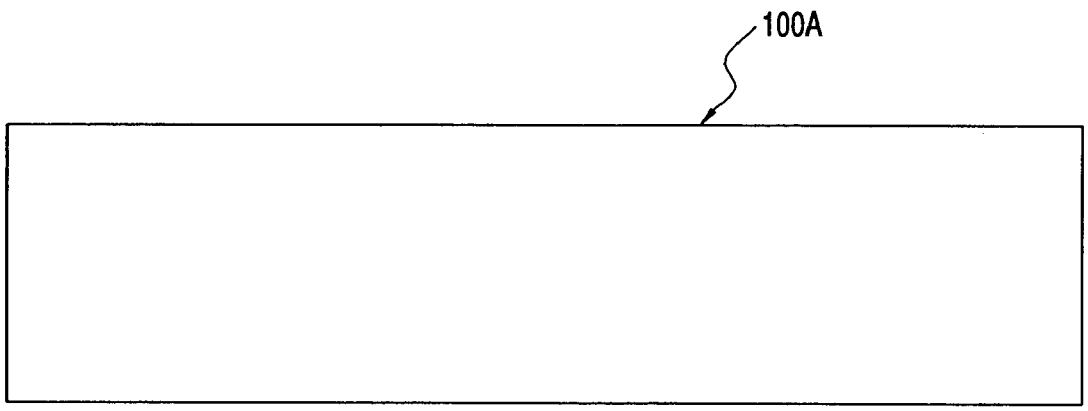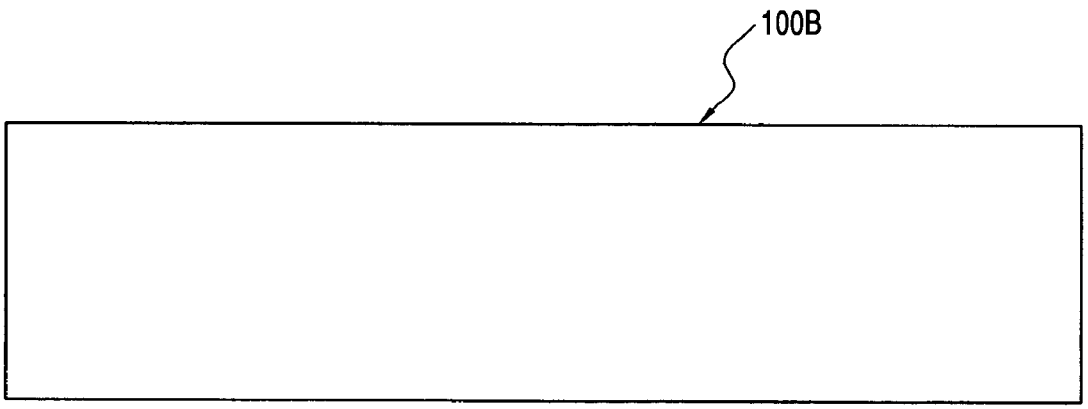
FIG.1

METHOD FOR FIELD-BASED ECOLOGICAL RISK ASSESSMENT USING RODENT SPERM-ANALYSIS

This application claims the benefit of U.S. provisional patent application Ser. No. 60/461,813, filed on Apr. 11, 2003 and U.S. provisional patent application Ser. No. 60/510,542, filed on Oct. 14, 2003. Each of the foregoing applications is incorporated herein by reference.

I. FIELD OF THE INVENTION

The present invention relates generally to ecological risk assessment. More specifically, the present invention relates to a method for performing rodent sperm analysis in field-based ecological risk assessment.

II. BACKGROUND OF THE INVENTION

Health risk assessments are used by many decision makers to determine the potential results of human and ecological exposure to contaminated substances. For example, concerned with potential fertility problems in military personnel, the United States Army has collaborated with the National Institute for Occupational Safety and Health to address the concern. An example of this is a study evaluating Vietnam War veterans who had been exposed to Agent Orange (Operation Ranch Hand). Another study was directed at the exposures of individuals to solvents and fuels during aircraft maintenance duties.

Typically, laboratory test results are combined with computer models that scale up the measured dose-response relationship to the level of the human or the ecological habitat. Field-testing the results of a health risk assessment has heretofore been considered impractical, considering that calculation-based risk assessments ordinarily project the health status of receptors over years or decades of exposure. Consequently, conducting field studies that would corroborate risk assessments would be costly in terms of time and resources.

The current state of practice in screening-level and baseline terrestrial ecological risk assessments (ERA) is the computation of model estimates, such as Hazard Quotients (HQs) for each of the various plants, invertebrates, birds, and mammals that inhabit a particular geographical site of interest. A hazard quotient, the ratio of an animal's estimated daily dietary doses of a chemical to a reputedly safe dose of the same chemical, has notable limitations. A hazard quotient can therefore serve only as a mere risk probability screening tool. Hazard quotients, by themselves, do not indicate that inhabitants at a geographical site of interest are at actual risk.

In most cases, ecological risk assessments only extend to the desktop calculation stage. Although guidance recommends that the field condition be assessed in order to verify the commonplace predictions of moderate to severe impacts accruing to the site biota, rarely do field studies proceed.

For example, ERA modeling is employed to anticipate toxicological effects occurring in the wild (that is, the field) based on a specified HQ level being exceeded. At present, the few field techniques that are available to be applied when working with field organisms, only measure chemical exposures as opposed to health effects. Examples include comparing chemical concentrations in animal and plant tissues of both the chemically-contaminated site and a matched (non-contaminated) reference location.

For example, it can be determined that the spleen of an animal trapped in a contaminated site contains thirty percent more of a toxic chemical than the spleen of an animal trapped at a corresponding reference site (that is, a non-contaminated site). One could wrongly conclude from such measurements, that due to their exposures, inhabitants of the contaminated site are likely to die prematurely or to develop health problems. Such conclusions are unsupported, because tissue concentration cannot be related to health effects. Thus, in the example offered, one would not be able to determine that an animal with thirty percent more of a toxic chemical in its spleen is unable to reproduce or is unable to carry on some other vital biological function. One might suspect that an animal with an excess of a chemical in one of its organs is unhealthy, but the measured chemical level does not prove this.

Similarly, one could measure the amount of a given enzyme present in animals that are exposed to a contaminated site, and also in animals of a noncontaminated reference location. Although animals from the contaminated site may have higher or lower levels of enzyme, there is no way to tell if the animals of the contaminated site are unhealthy.

As described above, although ERA modeling can serve as a risk screening tool, it cannot determine if actual effects are occurring in animals of the contaminated site. All current ERA health assessment measures do not have benchmarks or thresholds for effect, which if exceeded, would tell the risk assessor that effects are in fact occurring.

Thus, there does not currently exist a formal field-truthing methodology for the verification of modeled toxicological effects in terrestrial systems.

Therefore, what is needed is a field-truthing method that is capable of measuring practical toxicological effects in terrestrial systems. Such a method should validate laboratory studies and provide direct assessment of contaminated health impact. Such a method should also have a specific benchmark or threshold with which to measure in order to determine the practical toxicological effect in terrestrial systems.

III. SUMMARY OF THE INVENTION

The present invention provides a formal field-truthing methodology which documents the consequences of chemical exposure on reproductive endpoints, a very significant effect of chemical exposure. The methodology of the present invention is predicated on three principal assumptions. First, if after a specified period of time of being exposed to contaminated site media, animals fail to display physiological evidence of reproductive impact, it is reasonable to anticipate that future reproductive impacts will not arise. Second, it could be that the only difference between a contaminated site of interest and a corresponding reference site is soil chemistry. If there is a reduction in the quality of conventional sperm parameters (for example, sperm count, sperm motility, and sperm morphology), one can accurately conclude that the effects on the sperm are due to the chemical influences in the soil. Third, if small rodents at a contaminated site have impaired reproductive capability as determined by the sperm parameters, by implication, other site terrestrial ecological receptors have the potential to be experiencing similar reduced reproductive success.

The present invention is a method for assessing ecological impact to receptors. The vast majority of our understanding of chemical toxicity in humans derives from testing conducted with laboratory animals, principally the laboratory rat. For human health protection, the results of chemical exposures to rodents that are administered under artificial conditions in the laboratory are ordinarily relied upon. Comparing controlled laboratory conditions to actual field conditions on the same or similar species is a logical validation step and can be invaluable in determining the validity of exposure assumptions.

In the present invention, small animals are preferably trapped both at a contaminated site and at a corresponding reference trapping site. After the animals are trapped, sperm analysis is conducted for the animals trapped at both sites. In embodiments, the sperm analysis can be corroborated with additional data to further increase the accuracy of the comparison. Finally, as definitive a determination as is possible about the health or lack of health of the terrestrial site animals (principally mammals) at the contaminated site is developed.

An objective of the present invention is to make a determination about the reproductive health of terrestrial ecological receptors.

Another objective of the present invention is to document the consequences of chemical exposure on reproductive endpoints for small rodents.

Yet another objective of the present invention is to serve as a formal field-truthing methodology for the verification of modeled toxicological effects.

An advantage of the present invention is that it provides a method that can reliably indicate whether animals at a contaminated site have been harmed by chemicals present at the site.

Another advantage of the present invention is that it is less time consuming than conventional methods of ecological risk assessment.

Yet another advantage of the present invention is that it is more cost effective than conventional methods of ecological risk assessment.

Yet another advantage of the present invention is that it offers several advantages when combined with conventional approaches of study.

Yet another advantage of the invention is that for ecological assessments, it supplies the needed exit strategy for sites that would otherwise have an ongoing series of tests run.

Yet another advantage of the invention is that it can be applied at almost any soil-contaminated site with health risk assessment concerns, as it capitalizes on the ubiquitous distribution of small rodents.

Yet another advantage of the invention is that it employs sperm parameter testing which has proven to be a sufficiently sensitive measure.

Yet another advantage of the invention is that it is based on reproduction, which is reputedly the highest valued toxicological endpoint in ecological risk assessment.

Yet another advantage of the invention is that it can serve as a preventative maintenance tool in that the invention can provide an early indication of the potential for harmful effects to accrue to mammals such as humans before they enter a particular site.

Yet another advantage of the invention is that it provides a rapid turn-around of information.

Given the following enabling description of the drawings, the method of the present invention should become evident to a person of ordinary skill in the art.

IV. BRIEF DESCRIPTION OF THE DRAWINGS

Like reference numerals in the figures represent and refer to the same element or function.

FIG. 1 illustrates the testing sites involved in an embodiment of the present invention.

V. DETAILED DESCRIPTION OF THE DRAWINGS

Figure 2:
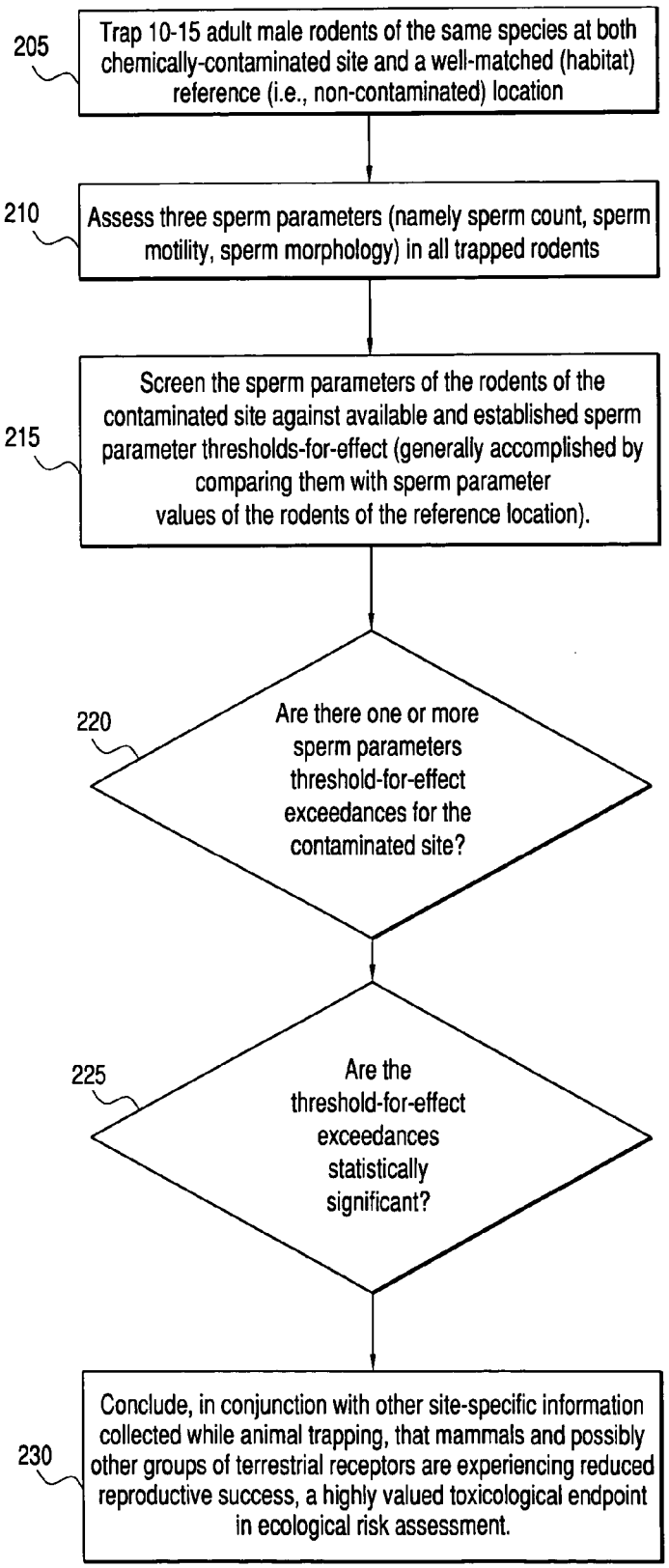
FIG. 2 depicts a flow diagram illustrating the steps involved in an exemplary embodiment of the present invention.

The present invention, known as Rodent Sperm Analysis (RSA) is a relatively direct method for measuring the potential effect of contamination in a suspected contaminated area. The method utilizes scientifically validated methods and provides better information for decision-makers to manage health risk. The RSA provides benefits in ecological health risk assessments at ranges and closing installations and has the potential to provide valuable options to active installations, soldier deployments, for example, and human health risk assessments.

The vast majority of the understanding of chemical toxicity in humans derives from testing conducted with laboratory animals, principally the laboratory rat. RSA reasoning is based on the fact that the results of chemical exposures to rodents that are administered under artificial conditions in the laboratory are relied upon for human health protection. Comparing controlled laboratory conditions to actual field conditions on the same or similar species is thus a logical validation step and can be invaluable in determining the validity of exposure assumptions.

Referring now to FIG. 1, contaminated site 100A is shown with reference site 100B. Small rodents (for example, mice, rats, voles, squirrels, and other similar viable mammalian species) are preferably concurrently trapped at these locations. Rodents are the perfect real-world, worst-case receptors of exposure. Where contamination exists (for example, in contaminated site 100A), rodents burrow in the contaminated soil, eat the contaminated vegetation, and drink the contaminated water. They typically do not migrate, and many generations of rodents live in the contaminated conditions year after year. Further, rodents reside in almost every habitat, are easy to trap, easy to handle, and represent a worst-case exposure scenario. Further, small rodents typically interact directly with the soil. Thus, they are more likely to come into contact with contaminants than other animals. Finally, small rodents are typically not protected by animal protection groups. Thus, the sacrifice of small rodents is more acceptable to the community than other animals. For example, mice are routinely sacrificed for experimental purposes.

If the findings of a Health Risk Assessment that relies on toxicological laboratory results do not match the conditions found in the rodents of an actual contaminated site (that is, the HRA predicts that site rodents are diseased, yet they are healthy and thriving), the HRA assumptions and results should be re-assessed. Cleanup decisions on an area that is showing no harm to generations of field mice may need to be reconsidered. People in such an environment may not need long term medical surveillance.

Contaminated site 100A may be a former battle site or target range where the soil has been contaminated with uranium or some other harmful substance. For example, contaminated site 100A may contain possibly dangerous levels of metals and/or explosives or other dangerous substances in the example illustrated in FIG. 1.

Unlike contaminated site 100A, reference site 100B does not include any harmful contaminants. The corresponding sites should be matched according to hydrology, soil, topography, site-use history, degree of maintenance, and/or plant community type. It should be noted that contaminated site 100A is distinct from reference site 100B, such that the home ranges of the rodents at each do not overlap. Otherwise, an inhabitant of a contaminated site may be visiting an uncontaminated site. Thus, in such an instance, a contaminated animal would be trapped on an uncontaminated site, and the accuracy of the analysis would be compromised.

It should be noted that the non-migratory nature of small rodents precludes the possibility that an inhabitant of a contaminated site may be visiting an uncontaminated site, for example.

Now referring to FIG. 2, a flowchart 200 representing the general operational flow is shown, according to an embodiment of the present invention. More specifically, flowchart 200 depicts an example control flow involved in executing the rodent sperm field analysis method of the present invention. Flowchart 200 begins with step 205.

In step 205, a representative sample of rodents (for example, 10-15 adult male rodents) of the same species is trapped or collected at the contaminated site (for example, a chemically-contaminated site). During the course of the field effort (for example, two weeks), an abundance of population data (for example, species diversity, population size, sex ratio, age distribution, etc.) is collected. This information will preferably be used to corroborate the findings of the sperm parameter analysis conducted for a contaminated site relative to a matched reference (non-contaminated) location.

The key for determining the number of rodents to trap is determining what the statistically significant number is, as is known by those of ordinary skill in the art. Likewise, a representative sample of rodents of the same species (for example, 10-15 adult male rodents) is trapped or collected at a well-matched reference site (that is, a non-contaminated site). As mentioned above, the corresponding sites should be matched according to hydrology, soil, and topography, etc. After all of the rodents are trapped, they are preferably euthanized with carbon dioxide. It should be noted that smaller rodents (for example, mice) are ideal for the method of the present invention due to their plentifulness in most habitats, ease of capture, approved euthanizing methods, and smaller home ranges or territories. Further, the smaller rodents tend to have the most direct contact with soil and are also more likely to be non-migratory in nature.

In step 210, sperm parameters of the rodents are assessed. As is known to those of ordinary skill in the relevant art, there is a definite relation between sperm quality and the ability of a rodent to reproduce. In other words, sperm motility, sperm count, and sperm morphology are each, well-established barometers of reproductive success. More specifically, a determination can be made as to how much of a reduction in the count and motility parameters and how much of an increase in the number of abnormally-shaped sperm will trigger reduced reproductive success. Thus, in at least one embodiment, sperm motility (ability of sperm to swim normally), sperm count, and sperm morphology (the percentage of misshapen sperm) may be assessed in all collected rodents (that is, monitoring the three sperm parameters to assess the potential of contaminated soils to function as reproductive toxicants in ecological receptors and humans).

To assess sperm motility, the right vas deferens may be surgically removed to minimize blood contamination. After excising tissue from the separated vas deferens, the tissue may be immediately placed into a pre-warmed suspension medium containing a chemical solution, as would be known to one of ordinary skill in the art. After a "swim-out" period in which sperm are allowed to enter the medium, a cannula can be inserted into the medium to obtain a sample. The cannula can then be inserted into the retractable stage of the HAMILTON THORNE INTEGRATED VISUAL OPTICS SYSTEM (IVOS®) SPERM ANALYZER, for a general examination of sperm on the analyzer's monitor. One of ordinary skill in the art would recognize that additional steps would be undertaken to complete the sperm analysis.

To assess sperm count, an epididymis (for example, the left epididymis) of the rodents may be removed. For example, a HAMILTON THORNE INTEGRATED VISUAL OPTICS SYSTEM (IVOS®)SPERM ANALYZER may be employed to conduct this type of sperm assessment, as would be known to one skilled in the art.

In step 215, the sperm parameters of the rodents of the contaminated site are screened against available and established sperm parameter thresholds-for-effect. This may be generally accomplished by comparing the sperm parameter values of the rodents of the contaminated site with sperm parameter values of the rodents of the reference location. For example, pair-wise statistical comparisons may be conducted between rodents of the contaminated site and rodents of the corresponding reference site. A statistical analysis of sperm parameter comparison may also be conducted by using the Wilcoxon rank sum test, for example. More specifically, this test may be used to compare means of sperm parameters, and body and normalized liver weights of the rodents.

In decision step 220, it is determined whether there are one or more sperm parameter threshold-for-effect exceedances for the contaminated site. For example, it may be determined that there is no threshold exceedance for rodents trapped at the contaminated site regarding sperm motility and sperm morphology. But it may be determined that the rodents trapped at the contaminated site may have a lesser sperm count (for example, a reduction of 16.7%). For example, numerous studies indicate that many species of rodents are robustly fertile, and that sperm count needs to be reduced approximately eighty percent or more before reproductive success is compromised. Thus, if a study reveals that sperm count in rodents trapped at the contaminated site is only reduced by forty percent when compared with the rodents of the uncontaminated reference location, for example, a threshold-for-effect will not have been shown to have been exceeded, and it cannot be determined that reproductive success will be compromised in these animals.

In decision step 225, it is determined whether any observed threshold-for-effect exceedances are statistically significant. For example, if it appears that the sperm motility threshold in the rodents of the contaminated site has been exceeded, a t-test can be conducted to determine if the means of the motility data of the contaminated site and that of the reference location are different enough so as to be ascribed to site chemistry and not to (random) chance. The p statistic is used in the statistical analysis, where $p \leq 0.05$ is significant. Changes in three parameters that will indicate compromised reproductive success if statistically significant may include the following: (1) a decrease of approximately 80-90% in the sperm count from the reference population is an indicator; (2) a decrease of about 40-50% in sperm motility from the "control-rate" is an indicator (The "control rate" is the condition in the animals of the non-contaminated site.) or a case of less than 37% motile sperm overall for the contaminated site; and (3) an increase in the percentage of abnormally-shaped sperm of 4% or more, relative to the control rate will be an indicator.

Finally, in step 230, in conjunction with other site-specific information collected while animal trapping at the sites, a conclusion is drawn that mammals and possibly other groups of terrestrial receptors are experiencing reduced reproductive success, which is a highly valued toxicological endpoint in ecological risk assessment. For example, if in addition to the sperm count at a contaminated site being nearly 80% reduced from the condition at the reference location, the total number of rodents trapped at a contaminated site was markedly less than at the reference location, the confidence in concluding that animals at the contaminated site are being reproductively compromised, would be bolstered.

A further conclusion regarding humans may be drawn by realizing that if the small rodents are not demonstrating reproductive impacts, it can be reasoned that other terrestrial receptors (for example, humans or other ecologically critical species) are also not experiencing compromised reproductive success. These other species (for example, humans) generally have much less direct contact with the ground and forage over distances that far exceed the contaminated land parcels. Finding that reproductive health impacts are absent in the chronically exposed animals (that is, the rodents) provides great confidence that a soldier, for example, digging foxholes during a long deployment, will not develop a reproductive health effect. Confidence in results is also increased because the rodents may easily reflect 100 generations of exposure, for example.

A trial experiment for the present invention was conducted at the Ravenna Army Ammunition Plant in rural northeastern Ohio to test the accuracy and reliability of the invention. Six former burning ground sites, which posed the greatest potential chemical stress to site receptors on the basis of HQ magnitude alone, were selected out of seventy burning ground sites at the installation. The sites were geographically distinct from each other, such that small rodent home ranges at each site did not overlap.

Figure 3:
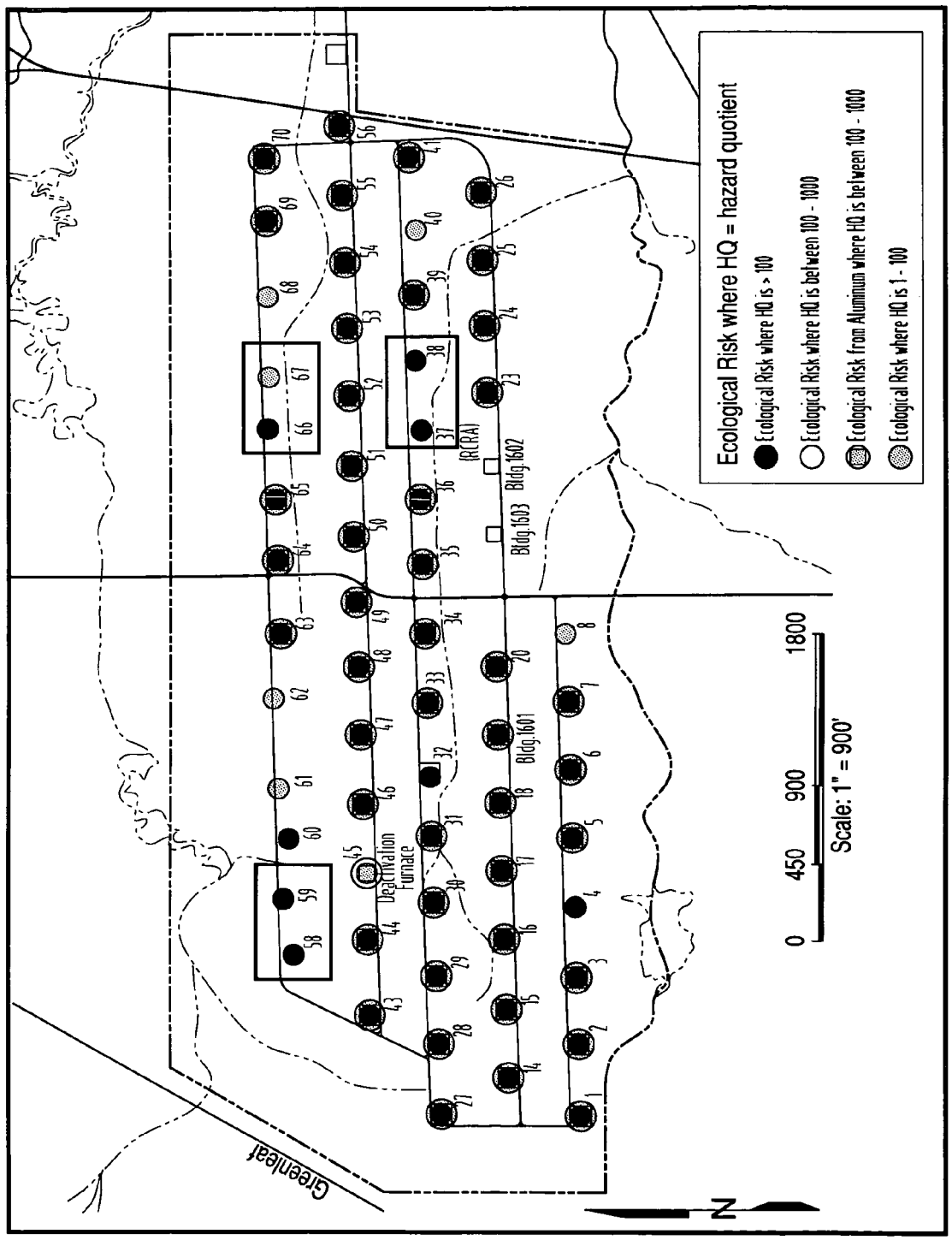
FIG. 3 illustrates an application of the invention according to an embodiment of the present invention.

Each study site consisted of two adjacent burning pads (pad pair numbers 37 and 38, 58 and 59, 66 and 67 in FIG. 3) that for multiple receptors, shared high HQs for either metals, explosives, or a mixture of these chemical groups. Corresponding reference sites (on the facility grounds but more than one mile beyond the burning pad area boundary) for each two-pad grouping were selected based on similar soil, site history and other characteristics, during a preliminary field reconnaissance effort in the spring of 2000. Specific criteria for selection included hydrology, soil type, topography, site-use history, degree of maintenance (that is, mowing), and plant community type. Care was taken to ensure that the reference sites offered the same level of resources as the study sites with regard to their ability to attract and support White-footed mice and Meadow voles and other animal life. An earlier small mammal survey indicated that White-footed mice and Meadow voles were the two most numerous small rodent species at the facility, although the survey had not been extended to the burning pad area.

Four consecutive trap nights at each of three sites (at a time) were envisioned, with the reasonable expectation that this would result in the minimum number of target animals (27 each of White-footed mice and Meadow voles for each site) being trapped to support a rigorous statistical comparison. The 27 adult males correspond to an alpha of 5%, a statistical power of 95%, and a 1:1 ratio of significant difference to coefficient of variation (CV). Employing this ratio, whereby the significant difference is selected relative to the CV rather than independent of it, allowed the sample size to be determined without knowing the measured CV for the sperm parameters from the field. Statistically for a normally distributed sperm parameter, the selection of 20% (of the parameter mean) as the significant difference, means that more than 99% of the results would fall within 2.5 standard deviations of the mean, and that one standard deviation would represent about 20% of the parameter's range.

Animal trapping began in mid-spring after the season's first litters had matured to adulthood (verifiable by pelage). Sherman live traps, baited with a rolled oats and peanut butter mix and a sweet feed mix for horses, were randomly placed in the preferable habitat within a 50-m radius from the center of each of the pads (three-pad pairs). Seventy-five traps were set out on each pad (150 per site), effectively saturating the trapping area. During the field effort, heavy rains flooded the soils of both the burning pad sites and the reference sites, causing rodents to migrate to higher ground and necessitating a delay of a second trapping event. All non-target animals trapped were identified to species, weighed using a Pesola scale, and released. All female juvenile and sub-adult White-footed mice and Meadow voles and juvenile males were weighed in the field and also marked on the top of the head with a small dab of colored nail polish prior to release, so that animals trapped on subsequent nights would not be double counted. Females were additionally assessed for reproductive state (lactating or pregnant). Although the conditions did not allow for the planned number of captures, a sufficient number of White-footed mice were collected from the sites.

Target animals (i.e., adult male White-footed mice and Meadow voles) were transported in their traps on the day following capture to the field laboratory. Target animals were euthanized with carbon dioxide, and liver weights were first recorded. For the assessment of sperm motility, the right vas deferens was surgically removed with care to minimize blood contamination. The excised tissue was immediately placed into a pre-warmed suspension medium containing 3 ml of phosphate buffered saline with 1% bovine serum albumin, and given a 3-minute "swim-out" period to allow sperm to enter the medium. A 100 mm cannula was then inserted into the medium to obtain a sample, and the cannula inserted into the retractable stage of a HAMILTON THORNE INTEGRATED VISUAL OPTICS SYSTEM (IVOS®) SPERM ANALYZER, for a general examination of sperm on the analyzer's main unit color monitor. The analyzer was preset to automatically move the stage to five different fields along the length of the cannula and to store each motion image (uniquely identified by study number, animal number, and cannula field number) on a write once optical disk, creating a permanent record for precise image reproduction and retrieval. Several weeks later, each image was recalled from the optical disk and analyzed for motile and non-motile cells.

A percent motility for all five recorded fields was determined for each animal, and other motility parameters (including straight-line, curvilinear, and path velocities; and progressive motility and cross-beat frequency) were also calculated. The left epididymis was also removed following animal euthanization, and frozen on dry ice. It was used to determine total sperm count and sperm abnormality (the percentage of misshapen sperm). The epididymis was thawed and the caudal section removed and weighed in order to report the total count as millions of sperm/gram of caudal epididymal tissue.

It was then homogenized and a 100 ml sample added to a vial containing a fluorescent dye (Hoechst dye H33342) to stain the DNA in the sperm head, in order to prevent surrounding debris from being counted as sperm. A 9 ml sample was added to a slide which was cover-slipped, secured to the retractable stage, and then loaded into the IVOS. The analyzer automatically counted the stained sperm heads for 20 fields per slide, minimizing the sperm cell distribution variance within single samples. For sperm morphology, two slides were prepared from the epididymal sample prior to homogenization, and later stained with 5% eosin and cover-slipped for microscopic evaluation. Two hundred sperm cells were evaluated with reverse phase/dark field microscopy (40× objective) for head and tail abnormalities (size, shape, and double heads/tails), with the results reported as the percentage of the 200 sperm that were abnormal. The procedures followed for the evaluation of sperm count, sperm motility, and sperm morphology are those of Pathology Associates, a Charles River Company 2002.

Due to the weather and reduced trapping success, there were not enough adult male White-footed mice to perform pair-wise statistical comparisons between burning pad pairs and corresponding reference sites as planned. The burning pads and the reference sites were each pooled to preserve statistical integrity (described below). It was only possible to statistically compare the sperm parameters of mice because of the low vole captures. Consistent with previous reports in the literature, the sperm parameter with the greatest variability, as illustrated by the CV in Table 1 (below), was sperm count. Table 1 reports the results of the Wilcoxon rank sum test comparing medians of sperm parameters, and body and normalized liver weights of the mice.

There was no statistically significant difference between burning pads and reference sites for either sperm parameter (sperm count and sperm motility; sperm abnormality was 0% for both groups), although the lesser sperm count of the burning pad mice (a reduction of 16.7%) was in the direction expected (that is, exposures to contaminants are known to reduce sperm production). However, variability of burning pad mice was less than the reference site mice, as demonstrated by a smaller range of values for two of the parameters (count and motility). The only attribute with a statistically significant difference was liver weight, with livers of mice from the burning pads 17.9% heavier than those of reference site mice. However, this difference disappears when the liver weight is normalized by body weight.

TABLE 1

Statistical analysis of sperm parameter comparison

| Sperm Parameter | Mean of Reference Areas | Mean of Burning Pads | Percent Difference[1] | Percent Difference/CV[2] | Agreement with Expected Direction of Difference[3] | Probability that Observed Difference Resulted From Chance[4] |
|---|---|---|---|---|---|---|
| Sperm Count | 1670 | 1409 | −16.71 | −0.78 | Yes | 0.114 |
| Sperm Motility | 98.4 | 99.2 | 0.84 | 0.55 | No | 0.093 |
| Sperm Abnormality | 0.0 | 0.0 | NA | NA | No | NA |

[1] calculated as mean of pooled burning pads minus mean of pooled reference areas/overall mean, multiplied by 100.
[2] calculated as the pooled standard deviation/overall mean.
[3] The expectation is that contaminants at the burning pads will reduce sperm count, reduce sperm motility, and increase the percentage of misshapen sperm.
[4] probability calculated using one-sided Wilcoxon Exact test assuming a power of 95%.

TABLE 2

Estimated probability to detect a difference between biological attributes

| Biological Attribute | Average Attribute Value Over All Areas | CV Over All Areas | Power at 5% ∀ Level | | | Power at 5% ∀ Level | | |
|---|---|---|---|---|---|---|---|---|
| | | | for Sig. Diff. equal to CV | for 20% Sig. Diff. | for 30% Sig. Diff. | for Sig. Diff. equal to CV | for 20% Sig. Diff. | for 30% Sig. Diff. |
| Sperm Count ($10^6$ sperm/g tissue) | 1558 | 21.55 | 53 | 48 | 77 | 68 | 64 | 88 |
| Motility (%) | 98.7 | 1.52 | 48 | 100 | 100 | 65 | 100 | 100 |
| Body Weight (grams) | 21.73 | 10.34 | 48 | 93 | 100 | 65 | 97 | 100 |
| Normalized Liver Weight[1] | 0.053 | 13.16 | 48 | 79 | 98 | 65 | 89 | 99 |

[1] Normalized liver weight as liver weight (grams)/body weight (grams).

The data was further evaluated to determine the minimum detectable difference between groups using the Wilcoxon Rank Sum Test. Table 2 (above) lists the biological attributes in order of decreasing power to detect a 20% difference between group means at an alpha of 5%. Power ranged from 100 to 91% for sperm morphology, motility, body weight, and liver weight, with the power decreasing as the CV increased, respectively. It was, therefore, possible to detect a minimum difference of 20% between groups for these four measures. A detectable difference of 20% was not possible for sperm count, which had a 48% power. However, the power to detect a minimum difference of 30% at an alpha of 5% for sperm count was 77%.

A total of 152 small mammals representing 10 species were captured in the study during the two trapping sessions of 8 and 6 days, respectively. The majority of these animals (58%) were target species. White-footed mice were present in nearly equal numbers at the burning pads and the reference sites, while Meadow voles were five times more numerous at the burning pad sites. The reference sites had four non-target species present that were absent from the burning pads, and the burning pad sites had two non-target species present that were absent from the reference sites. For four of these non-target species, only one or two individuals constituted the captures. The greatest disparity in species composition between the burning pads and the reference sites, were captures only at the reference sites of Short-tailed shrews and Eastern chipmunks.

The animal capture information can be used to support the information provided by the primary assessment (that is, sperm parameter) metrics. The capture information indicates that the key species are not being excluded from, and are not avoiding the burning pads, reputedly one of the most contaminated portions of the facility. Although the captured animal numbers are small, the field measurements show that females are not any less reproductively active at the burning pads than at the reference sites, based on the percentages of lactating and pregnant individuals. Results of the sperm analysis show that male White-footed mice are not reproductively impaired, because there were no statistically significant differences (P>0.05) between groups (that is, count and motility). The CVs for all three sperm parameters of mice trapped at both the burning pads and the reference sites are consistent with those reported in the literature for rodents, with the count being the most variable, motility having only slight variability, and an abnormality rate as low as 1%. Because rodents produce 10-20 times more sperm than needed to ensure full reproductive success, it is a safe assumption that the approximate 17% reduction in the sperm count of the burning pad mice is inconsequential, even had the difference been statistically significant. Collectively, the trapping results and sperm parameters for mice mean reproductive success for these terrestrial receptors in the burning pad areas.

Results from the rodent sperm analysis method's experimental use allowed for arriving at a determination of acceptable risk for mammals at the burning pads. Although desirable numbers of target animals were not captured, the small CVs for the sperm parameters allowed good statistical confidence in the study results. The results indicated that reproductive effects, as an assessment endpoint, were not evident in the exposed population despite the fact that the HQ calculations of the initial desktop assessment had indicated otherwise.

The finding of no unacceptable risk lends support to those contentions that ecological HQs are misleading numbers because they overestimate the prevalence of toxicological effects in the field. The results also suggest that there is more to be gained by advancing to the field for a verification endeavor, rather than conducting mathematically focused second and third tier ERAs. Although small mammals at the contaminated sites did not display any adverse reproductive effects, a significant difference ($p \leq 0.05$) in liver weights was evident. When liver weights were normalized to body weight, however, differences were not evident. Regardless, fresh liver weights in captured small rodents is useful as a measure of exposure, and liver measurement is preferably included as a fixed component of the method.

It is believed that at sites where the in-place contamination is one or more decades old, and where birds and mammals consequently have had multigenerational exposures, detrimental effects should be either present or not present. In the latter case, such effects either never occurred, or did first occur but were followed by a period of ecological recovery. The pilot study was designed to detect critical detrimental (that is, reproductive) effects if such were present. Based on the study's outcome, a conclusion is drawn that the method represents a reasonable, practical and cost-attractive field oriented technique. The field method allows for much better closure on animal aspects of ERA risk than depending on HQs and other mathematical predictions.

Of the three sperm parameters evaluated, only sperm count differed between the contaminated site and reference location animals. Specifically, reference location mice had a sperm count reduction of 16.7% when compared with mice of the reference location.

Results from the Ravenna study allowed for the determination of acceptable risk for mammals at the burning pad sites. The study indicated that reproductive effects, as an assessment endpoint, were not evident in the exposed population despite the fact that the HQ calculations of the initial desktop assessment had indicated otherwise. The finding of no unacceptable risk lends support to those contentions that ecological HQs are misleading numbers because they overestimate the prevalence of toxicological effects in the field. The field method of the present invention allows for much better closure on animal aspects of ERA risk than depending on HQs and other mathematical predictions.

A second trial experiment for the present invention was conducted at the Jefferson Proving Ground in Madison, Ind. to further test the accuracy and reliability of the invention. Just as in the first trial experiment, two sites were chosen (that is, a reference site and a study site).

In the second trial experiment, *Microtus Pennsylvanicus* (Meadow vole) was captured in Sherman live traps on uranium depleted (DU) and high explosive (HE) impact areas (that is, the study sites) from Sep. 19-24, 2002 and on the reference (DA) areas from Oct. 10-15, 2002. Adult male animals were identified and submitted for sperm analysis. All animals submitted for sperm analysis were euthanized with carbon dioxide inhalation and exsanguination. After euthanasia, a terminal body weight for each animal was measured and recorded. For all animals, the abdominal cavity was opened and the reproductive organs exposed. For motility assessment, the right epididymis was dissected away from the testis and immediately placed in a petri dish containing 3 mL of a solution consisting of 1% Bovine Serum Albumin dissolved in Phosphate Buffered Saline. The solution was prewarmed to a temperature of approximately 38° C. The epididymis was pierced and a minimum 3-minute period was allowed for the sperm to disperse from the epididymis.

The liver, spleen, kidneys and testes were removed from the body, weighed and preserved in 10% neutral buffered formalin (NBF). The left epididymis was removed and the caudal section was trimmed and weighed. The left cauda epididymis was then placed in a petri dish containing 3 mL of deionized water and used to determine total sperm count.

To evaluate sperm motility, following the dispersal period, a 9 μL sperm sample was obtained from the petri dish and loaded into a 20 μM deep Cell-Vu chamber. The chamber was cover slipped and immediately loaded onto the prewarmed stage of the Hamilton Thorne IVOS automated sperm analyzer. Five fields were automatically selected by the analyzer and each motion image was recorded and stored digitally. The images were subsequently analyzed for percent motility. The percent progressive motility and the sperm motion parameters listed in Table 3 (below) were also obtained for each animal. The images were permanently stored to optical media.

TABLE 3

Sperm Motility Evaluation Parameters

| Sperm Parameter | Definition |
|---|---|
| Motility | The ratio (%) of moving sperm to total sperm present. |
| Progressive Motility | The ratio (%) of sperm that meet a minimum velocity (75 μM/sec). |
| Path Velocity (VAP) | Velocity of the average cell path. |
| Straight-line Velocity (VSL) | Velocity from the beginning of the sperm track to the end of the track. |
| Curvilinear Velocity (VCL) | Velocity of the actual path (point-to-point). |
| Beat Cross Frequency (BCF) | The frequency with which the sperm track crosses the sperm path. |

To evaluate sperm motility, following the dispersal period, a 9 μL sperm sample was obtained from the petri dish and loaded into a 20 μM deep Cell-Vu chamber. The chamber was cover slipped and immediately loaded onto the prewarmed stage of the HAMILTON THORNE IVOS® AUTOMATED SPERM ANALYZER. Five fields were automatically selected by the analyzer and each motion image was recorded and stored digitally. The images were subsequently analyzed for percent motility. The percent progressive motility and the sperm motion parameters listed in Table 3 (below) were also obtained for each animal. The images were permanently stored to optical media.

To evaluate sperm morphology, two eosin stained slides were prepared for each animal from the epididymis total count preparation. The slides were evaluated and a minimum of 200 sperm cells/animal were examined for morphological development.

In addition to the above evaluations, tissue histopathological evaluation was conducted. The preserved tissues (liver, spleen, kidneys and testes) were transferred for processing and evaluation. The tissues were embedded in paraffin, sectioned at approximately five microns, stained with hematoxiylin and eosin (H&E), and examined by a veterinary pathologist. The technical qualities of tissue fixation, microtomy and staining for the majority of tissues were determined to be good. Autolysis and/or fixation artifacts were present in most sections of testes. In addition, staining of testes sections was not optimal for spermatogenic staging.

Statistical analysis was also conducted. Thus, the means and standard deviations for the animal body weight data, the organ-to-body weight ratios (as a percent of body weight), the sperm motility and motion data, the total count data and the sperm morphology data were calculated. Summary data for the impact areas (DU and HE) were reported combined (DU&HE) and separately. Data were grouped by parameter and tested for normality of distribution using the Shapiro-Wilk test. Normally distributed data was analyzed by analysis of variance (ANOVA). If a significant effect was seen ($p<0.05$), the Dunnett's test was used for comparison of the impact groups (DU and HE) to the reference group (DA). Data failing the Shapiro-Wilk test were analyzed by the Kruskal-Wallis nonparametric test. If a significant effect was seen ($p<0.05$), the Mann-Whitney U test was used for comparison of the impact groups (DU and HE) to the reference group (DA). Histopathological findings were not statistically analyzed. Statistical analyses were performed using verified SAS computer programs.

Results of the trial experiment were divided into three groups: (1) body and organ weights, (2) sperm analysis parameters; and (3) microscopic tissue evaluation.

Regarding body and organ weights, a statistically significant decrease in the liver-to-body weight ratio was observed in the combined impact area data (DU+HE) compared to the reference area data (DA). A similar and corresponding decrease in the liver-to-body weight ratio was not observed when the impact areas were separated. No other statistically significant differences or biologically meaningful differences were observed in the body weight or relative organ weight data, including spleen, kidney, left epididymis and testes, for the combined or separated impact areas.

Regarding sperm analysis parameters, statistically significant reduction of the curvilinear velocity (VCL) for the high explosive (HE) impact area was observed. A similar, although not statistically significant, reduction in the straight-line (VSL) and average path (VAP) velocities was also observed. No biologically meaningful differences were observed for the sperm analysis parameters examined, including sperm motility, progressive motility, VAP, VCL, VSL, BCF, epididymal sperm count or sperm morphology, either as combined or separated impact areas. Tables 4-7 (below) show the results relating to sperm analysis parameters.

TABLE 4

SUMMARY OF SPERM ANALYSIS PARAMETERS
IMPACT AREAS COMBINED

| | | AREA GROUPING: | |
|---|---|---|---|
| | | DA (REFERENCE) | DU + HE[a] (IMPACT) |
| MOTILITY (% MOTILE) | MEAN[x] | 76 | 80 |
| | SD | 17 | 11 |
| | N | 10 | 14 |
| PROGRESSIVE MOTILITY (% PROGRESSIVELY MOTILE) | MEAN[x] | 67 | 71 |
| | SD | 16 | 12 |
| | N | 10 | 14 |
| VAP (μm/sec) | MEAN[x] | 230.1 | 194.7 |
| | SD | 18.3 | 54.5 |
| | N | 10 | 14 |

TABLE 4-continued

SUMMARY OF SPERM ANALYSIS PARAMETERS IMPACT AREAS COMBINED

| | | AREA GROUPING: | |
|---|---|---|---|
| | | DA (REFERENCE) | DU + HE[a] (IMPACT) |
| VCL (μm/sec) | MEAN[x] | 478.0 | 408.8 |
| | SD | 36.8 | 108.6 |
| | N | 10 | 14 |
| VSL (μm/sec) | MEAN | 158.9 | 138.3 |
| | SD | 12.0 | 35.1 |
| | N | 10 | 14 |
| BCF | MEAN[x] | 26.5 | 29.6 |
| | SD | 3.2 | 10.1 |
| | N | 10 | 14 |
| EPIDIDYMAL SPERM COUNT (10[6] SPERM/GRAM OF TISSUE) | MEAN[x] | 2498.6 | 1902.4 |
| | SD | 499.1 | 799.3 |
| | N | 10 | 14 |
| MORPHOLOGY[b] (% ABNORMAL SPERM) | MEAN[x] | 0.9 | 0.8 |
| | SD | 0.7 | 1.0 |
| | N | 10 | 11 |

[a]DATA FOR HE AND DU IMPACT AREAS COMBINED.
[b]MEAN AND STANDARD DEVIATIONS WERE CALCULATED USING THE TOTAL NUMBER OF ABNORMAL SPERM AS A PERCENTAGE OF THE NUMBER OF SPERM EXAMINED.
[x]DATA ARE NOT NORMALLY DISTRIBUTED (SHAPIRO-WILK TEST p < 0.05).
NONE STATISTICALLY DIFFERENT FROM DA (REFERENCE) GROUP.

TABLE 5

SUMMARY OF SPERM ANALYSIS PARAMETERS IMPACT AREAS SEPARATED

| | | AREA GROUPING: | | |
|---|---|---|---|---|
| | | DA (REFERENCE) | DU (IMPACT) | HE (IMPACT) |
| MOTILITY (% MOTILE) | MEAN[x] | 76 | 73 | 84 |
| | SD | 17 | 14 | 7 |
| | N | 10 | 5 | 9 |
| PROGRESSIVE MOTILITY (% PROGRESSIVELY MOTILE) | MEAN[x] | 67 | 63 | 76 |
| | SD | 16 | 9 | 10 |
| | N | 10 | 5 | 9 |
| VAP (μm/sec) | MEAN[x] | 230.1 | 227.2 | 176.6 |
| | SD | 18.3 | 28.8 | 58.3 |
| | N | 10 | 5 | 9 |
| VCL (μm/sec) | MEAN[x] | 478.0 | 478.3 | 370.2[z] |
| | SD | 36.8 | 47.4 | 115.6 |
| | N | 10 | 5 | 9 |
| VSL (μm/sec) | MEAN | 158.9 | 149.2 | 132.2 |
| | SD | 12.0 | 29.4 | 38.1 |
| | N | 10 | 5 | 9 |
| BCF | MEAN[x] | 26.5 | 24.9 | 32.3 |
| | SD | 3.2 | 5.5 | 11.4 |
| | N | 10 | 5 | 9 |
| EPIDIDYMAL SPERM COUNT (10[6] SPERM/GRAM OF TISSUE) | MEAN[x] | 2498.6 | 1866.9 | 1922.1 |
| | SD | 499.1 | 737.6 | 874.6 |
| | N | 10 | 5 | 9 |
| MORPHOLOGY[a] (% ABNORMAL SPERM) | MEAN[x] | 0.9 | 1.4 | 0.3 |
| | SD | 0.7 | 1.1 | 0.6 |
| | N | 10 | 5 | 6 |

[a]MEAN AND STANDARD DEVIATIONS WERE CALCULATED USING THE TOTAL NUMBER OF ABNORMAL SPERM AS A PERCENTAGE OF THE NUMBER OF SPERM EXAMINED.
[x]DATA ARE NOT NORMALLY DISTRIBUTED (SHAPIRO-WILK TEST p < 0.05).
[z]KRUSKAL-WALLIS/MANN-WHITNEY U TEST SIGNIFICANTLY DIFFERENT FROM DA (REFERENCE) GROUP (p < 0.05).

TABLE 6

INDIVIDUAL SPERM MOTILITY AND TOTAL COUNT DATA

| UNIQUE ANIMAL ID | ANIMAL ID | PERCENT MOTILITY | PROGRESSIVE MOTILITY | VAP | VCL | VSL | BCV | TOTAL[a] SPERM COUNT |
|---|---|---|---|---|---|---|---|---|
| *DA AREA (REFERENCE SITE)* | | | | | | | | |
| 16 | MV-DA-3-34 | 92 | 84 | 189.6 | 400.5 | 131.6 | 20.7 | 2671.4 |
| 18 | MV-DA-2-30 | 75 | 65 | 242.5 | 495.4 | 174.4 | 30.2 | 1527.0 |
| 20 | MV-DA-3-84 | 37 | 30 | 256.2 | 543.3 | 160.3 | 28.1 | 2282.6 |
| 21 | MV-DA-3-34 | 78 | 71 | 225.1 | 476.4 | 162.7 | 22.6 | 2742.7 |
| 22 | MV-DA-3-78 | 88 | 78 | 219.6 | 450.2 | 157.2 | 24.7 | 2390.4 |
| 23 | MV-DA-2-81 | 85 | 71 | 243.3 | 494.9 | 156.4 | 26.9 | 3156.8 |
| 24 | MV-DA-3-58 | 78 | 69 | 241.3 | 480.8 | 174.6 | 30.9 | 2355.7 |
| 25 | MV-DA-1-45 | 83 | 74 | 220.2 | 462.6 | 162.2 | 25.9 | 2338.7 |
| 26 | MV-DA-1-66 | 87 | 79 | 231.6 | 480.2 | 154.7 | 28.1 | 3276.9 |
| 27 | MV-DA-1-88 | 58 | 51 | 231.6 | 495.4 | 154.8 | 27.0 | 2243.7 |
| *DU AREA (IMPACT SITE)* | | | | | | | | |
| 1 | MV-DU-3-75 | 77 | 64 | 247.0 | 507.7 | 151.5 | 26.2 | 755.7 |
| 5 | MV-DU-1-57 | 49 | 48 | 256.8 | 514.0 | 195.6 | 33.3 | 1462.2 |
| 8 | MV-DU-4-71 | 82 | 70 | 182.5 | 396.4 | 115.1 | 19.6 | 2288.4 |
| 12 | MV-DU-4-51 | 84 | 71 | 228.5 | 488.9 | 145.5 | 24.8 | 2439.1 |
| 15 | MV-DU-1-43 | 73 | 60 | 221.0 | 484.6 | 138.5 | 20.4 | 2389.2 |
| *HE AREA (IMPACT SITE)* | | | | | | | | |
| 2 | MV-HE-3-82 | 76 | 70 | 234.5 | 434.8 | 188.1 | 27.5 | 2267.8 |
| 3 | MV-HE-2-44 | 85 | 54 | 83.0 | 173.7 | 71.5 | 46.3 | 958.8 |
| 4 | MV-HE-3-22 | 93 | 80 | 222.4 | 444.2 | 155.3 | 30.1 | 1590.5 |
| 7 | MV-HE-4-24 | 87 | 83 | 94.2 | 245.7 | 81.8 | 48.6 | 373.4 |

TABLE 6-continued

INDIVIDUAL SPERM MOTILITY AND TOTAL COUNT DATA

| UNIQUE ANIMAL ID | ANIMAL ID | PERCENT MOTILITY | PROGRESSIVE MOTILITY | MOTION PARAMETERS | | | | TOTAL[a] SPERM COUNT |
|---|---|---|---|---|---|---|---|---|
| | | | | VAP | VCL | VSL | BCV | |
| 9 | MV-HE-1-87 | 80 | 78 | 205.9 | 447.3 | 136.1 | 23.1 | 2262.6 |
| 10 | MV-HE-1-95 | 80 | 80 | 188.2 | 407.9 | 144.3 | 24.2 | 2684.4 |
| 11 | MV-HE-4-4 | 92 | 87 | 138.1 | 261.4 | 122.5 | 45.8 | 2452.9 |
| 13 | MV-HE-1-52 | 91 | 83 | 186.9 | 393.9 | 121.2 | 19.6 | 3132.5 |
| 14 | MV-HE-1-43 | 72 | 68 | 236.3 | 522.9 | 168.7 | 25.2 | 1575.7 |

[a]MILLION SPERM/GRAM TISSUE.

TABLE 7

INDIVIDUAL SPERM MORPHOLOGY DATA

| UNIQUE ANIMAL ID | ANIMAL ID | Normal | Head | | | | Tail | | | |
|---|---|---|---|---|---|---|---|---|---|---|
| | | | Amorphous | Small | Enlarged | Double | Coiled | Bent | Double | Other |
| *DA AREA (REFERENCE SITE)* | | | | | | | | | | |
| 16 | MV-DA-3-34 | 200 | 0 | 0 | 0 | 0 | 0 | 0 | 0 | 0 |
| 18 | MV-DA-2-30 | 197 | 3 | 0 | 0 | 0 | 0 | 0 | 0 | 0 |
| 20 | MV-DA-3-84 | 197 | 1 | 2 | 0 | 0 | 0 | 0 | 0 | 0 |
| 21 | MV-DA-3-34 | 198 | 1 | 1 | 0 | 0 | 0 | 0 | 0 | 0 |
| 22 | MV-DA-3-78 | 200 | 0 | 0 | 0 | 0 | 0 | 0 | 0 | 0 |
| 23 | MV-DA-2-81 | 196 | 4 | 0 | 0 | 0 | 0 | 0 | 0 | 0 |
| 24 | MV-DA-3-58 | 200 | 0 | 0 | 0 | 0 | 0 | 0 | 0 | 0 |
| 25 | MV-DA-1-45 | 199 | 0 | 0 | 1 | 0 | 0 | 0 | 0 | 0 |
| 26 | MV-DA-1-66 | 198 | 2 | 0 | 0 | 0 | 0 | 0 | 0 | 0 |
| 27 | MV-DA-1-88 | 198 | 1 | 1 | 0 | 0 | 0 | 0 | 0 | 0 |
| *DU AREA (IMPACT SITE)* | | | | | | | | | | |
| 1 | MV-DU-3-75 | 196 | 1 | 1 | 0 | 0 | 2 | 0 | 0 | 0 |
| 5 | MV-DU-1-57 | 199 | 1 | 0 | 0 | 0 | 0 | 0 | 0 | 0 |
| 8 | MV-DU-4-71 | 198 | 2 | 0 | 0 | 0 | 0 | 0 | 0 | 0 |
| 12 | MV-DU-4-51 | 199 | 1 | 0 | 0 | 0 | 0 | 0 | 0 | 0 |
| 15 | MV-DU-1-43 | 194 | 6 | 0 | 0 | 0 | 0 | 0 | 0 | 0 |
| *HE AREA (IMPACT SITE)* | | | | | | | | | | |
| 2 | MV-HE-3-82 | 199 | 1 | 0 | 0 | 0 | 0 | 0 | 0 | 0 |
| 3 | MV-HE-2-44 | | | | | | | | | |
| 4 | MV-HE-3-22 | 200 | 0 | 0 | 0 | 0 | 0 | 0 | 0 | 0 |
| 7 | MV-HE-4-24 | | | | | | | | | |
| 9 | MV-HE-1-87 | 200 | 0 | 0 | 0 | 0 | 0 | 0 | 0 | 0 |
| 10 | MV-HE-1-95 | 200 | 0 | 0 | 0 | 0 | 0 | 0 | 0 | 0 |
| 11 | MV-HE-4-4 | | | | | | | | | |
| 13 | MV-HE-1-52 | 197 | 2 | 0 | 1 | 0 | 0 | 0 | 0 | 0 |
| 14 | MV-HE-1-43 | 200 | 0 | 0 | 0 | 0 | 0 | 0 | 0 | 0 |

Regarding Microscopic Tissue Evaluation, no significant differences in the microscopic findings were noted in the liver, spleen, kidneys and testes between the impact and the reference area animals. Incidental, background and/or parasitic findings were noted in all tissues and in all areas. Minimal inflammation is a common liver finding in rodents and parasitic cysts were noted in livers of two reference voles. Extramedullary hematopoiesis (EMH) was absent or unidentifiable in the spleens of 6/14 impact animals and 2/10 reference animals. EMH is common in mouse spleens and its absence suggests a possible alteration in the ability to produce or the need for new blood cells. Additional diagnosis wais unobtainable with the tissues provided. Inflammation and degenerative tubular changes of minimal or mild severity are common in rodent kidneys and were present in both reference and impact animals. Degenerative changes in the seminiferous tubules were present in both reference and impact animals. Generally, these changes were minimal in severity and located near the rete testes. Most likely these areas of the seminiferous tubules represent the tubuli recti in which germinal epithelial cell loss is normal. Degenerative tubular changes were more severe in three of the impact voles evaluated. There was no apparent microscopic changes in the tissues examined that can be directly linked to exposure to (HE) or (DU) environments.

The second trial experiment showed that there were no exposure-related changes to body weight, organ-to-body weight ratios, sperm analysis parameters or microscopic evaluation of selected tissues. Incidental changes occurred in all areas (weight, sperm analysis and histopathological evaluation), but none were consistent between the impact exposure areas (HE, DU or HE+DU). Incidental changes included a decrease in the liver-to-body weight ratio of the combined (HE+DU) impact areas; however, a corresponding decrease was not observed when the impact data was separated by contaminant (HE or DU). Incidental changes in the sperm analysis parameters included a reduction in the curvilinear velocity (VCL), straight-line velocity (VSL) and average path velocity (VAP) for the HE impact area. These reductions were not considered exposure-related because progressive motility, of which velocity and straightness are components, was not reduced. In fact, the percent progressive motility for the HE impact area was equivalent to the reference. There were incidental microscopic findings in all tissues of all exposure areas.

One may conclude that high explosives (HE) or depleted uranium (DU) at the proving ground did not have an adverse impact on the body weight, organ-to-body weight ratio, sperm analysis parameters or microscopic cellular structure for the Meadow voles examined.

In addition to the two trial experiments conducted above, there were three other trial experiments conducted in other geographical areas for a variety of types of animal species. The results of these experiments are shown in table 8 below. The results include the studies at Ravenna and Madison for comparison purposes.

Those skilled in the art will appreciate that various adaptations and modifications of the above-described embodiments can be configured without departing from the scope and spirit of the present invention. Therefore, it is to be understood that, within the scope of the appended claims, the invention may be practiced and constructed other than as specifically described herein.

I claim:

1. A method for assessing ecological risk to mammals, comprising:
    collecting a representative sample of rodents from a contaminated site, wherein the rodents reflect generations of exposure to the contaminated site;
    collecting a representative sample of rodents from an animal reference site;
    comparing sperm count, sperm motility, and sperm morphology of the rodents from the contaminated site with the rodents from the animal reference site;
    determining whether the comparison between the sperm count, sperm motility, and sperm morphology of the rodents from the contaminated site and of the rodents from the animal reference site exceeds sperm parameter benchmarks for sperm count, sperm motility, and sperm morphology, thereby indicating if the rodents from the contaminated site have compromised reproductive success, wherein a decrease of approximately 80% to 90% in sperm count indicates comprised reproductive success; and
    making a determination about whether an ecological risk to terrestrial site mammals at the contaminated site is present or not based on whether said comparison exceeds the sperm parameter benchmarks.

TABLE 12

Rodent Sperm Analysis Results

| Army Study Site | Rodent Species Evaluated | Sperm Count Was count reduced at the affected site? (Y/N) | Percent count reduction in "site" rodents | Was biological threshold exceeded? (Y/N) | Sperm Motility Was biological threshold exceeded? (Y/N) | Sperm Morphology Was biological threshold exceeded? (Y/N) |
| --- | --- | --- | --- | --- | --- | --- |
| Ravenna Army Ammunition Plant, Ravenna, OH | White-footed mouse | Yes | 16.71 | No | No | No |
| Fort Bliss, El Paso, TX | Pocket mouse | Yes | 31.4 | No | No | No |
| | Kangaroo rat | Yes | 55.7 | No | No | No |
| Jefferson Proving Ground, Madison, Indiana | White-footed mouse | Yes | 23.9 | No | No | No |
| | | — | — | — | — | — |
| | | Yes | 25.3 | No | No | No |
| Fort Polk, Leesville, LA | Hispid cotton rat | Yes | 15.6 | No | No | No |
| Longhorn Army Ammunition Plant, Karnack, TX | Hispid cotton rat | Yes | data under review | No | No | No |
| | White-footed mouse | Yes | data under review | No | No | No |

2. A method according to claim 1, wherein a decrease of about 40% to 50% in sperm motility indicates comprised reproductive success.

3. A method according to claim 1, wherein an increase of 4% or more of abnormally-shaped sperm indicates comprised reproductive success.

4. The method of claim 1, further comprising corroborating the sperm count, sperm motility, and sperm morphology of the rodents from the contaminated site and of the rodents from the animal reference site with population data.

5. The method of claim 4, wherein the population data relates to species diversity.

6. The method of claim 4, wherein the population data relates to population size.

7. The method of claim 4, wherein the population data relates to sex ratio.

8. A method according to claim 1, further comprising corroborating the comparison between the sperm count, sperm motility, and sperm morphology of the rodents from the contaminated site and of the rodents from the animal reference site with data relating to female reproductive state.

9. The method of claim 8, wherein the data relates to pregnancy.

10. A method according to claim 1, wherein the contaminated site is contaminated with uranium.

11. A method according to claim 1, wherein the contaminated site is contaminated with explosives.

12. A method according to claim 1, wherein the rodents from the contaminated site reflect one hundred generations of exposure to the contaminated site.

13. The method of claim 8, wherein the data relates to lactation state.

14. A method for assessing ecological risk to mammals, comprising:
   collecting a sample of rodents from a contaminated site, wherein the rodents reflect generations of exposure to the contaminated site;
   collecting a sample of rodents from a reference site;
   comparing sperm count, sperm motility, and sperm morphology of the rodents from the contaminated site with the rodents from the reference site;
   determining whether the comparison between the sperm count, sperm motility, and sperm morphology of the rodents from the contaminated site and of the rodents from the reference site exceeds one or more sperm parameter thresholds-for-effect, thereby indicating if the rodents from the contaminated site have compromised reproductive success; and
   making a determination about whether an ecological risk to mammals at the contaminated site is present or not based on whether said comparison exceeds the sperm parameter thresholds-for-effect.

15. A method according to claim 14, further comprising comparing organ-to-body weight ratios of the rodents from the contaminated site with the rodents from the animal reference site to determine if there is a statistically significant decrease for the rodents from the contaminated site thereby establishing an exposure-related change.

16. A method according to claim 14, further comprising matching the reference site and the contaminated site according to hydrology, soil, and topography.

17. A method according to claim 14, wherein said mammals comprise rodents.

18. A method according to claim 14, wherein said mammals comprise mice, rats, voles, or squirrels.

19. A method according to claim 14, wherein sperm count and sperm motility are measured with a visual optics sperm analyzer.

20. A method according to claim 14, wherein said comparing comprises conducting pair-wise statistical comparisons of sperm count, sperm motility, and sperm morphology between rodents of the contaminated site and rodents of the reference site.

21. A method according to claim 14, wherein
   if the rodents at the contaminated site do not demonstrate compromised reproductive success, it is concluded that other mammals at the contaminated site are not experiencing compromised reproductive success; and
   if the rodents at the contaminated site demonstrate compromised reproductive success, it is concluded that other mammals at the contaminated site have the potential to experience compromised reproductive success.

22. A method according to claim 14, wherein a decrease of approximately 80% to 90% in sperm count, a decrease of about 40% to 50% in sperm motility, and an increase of 4% or more of abnormally-shaped sperm indicates comprised reproductive success.

* * * * *